United States Patent [19]

Wiezer et al.

[11] 4,433,145

[45] Feb. 21, 1984

[54] TRIAZINE STABILIZERS

[75] Inventors: Hartmut Wiezer, Gersthofen; Gerhard Pfahler, Augsburg, both of Fed. Rep. of Germany

[73] Assignee: Hoechst Aktiengesellschaft, Frankfurt, Fed. Rep. of Germany

[21] Appl. No.: 203,236

[22] Filed: Nov. 3, 1980

[30] Foreign Application Priority Data

Nov. 6, 1979 [DE] Fed. Rep. of Germany ....... 2944729

[51] Int. Cl.³ ............................................ C07D 401/14
[52] U.S. Cl. .................................................... 544/198
[58] Field of Search ................................ 544/212, 198

[56] References Cited

U.S. PATENT DOCUMENTS

| | | | |
|---|---|---|---|
| 4,028,334 | 6/1977 | Chalmers et al. | 544/198 |
| 4,033,957 | 7/1977 | Hofer et al. | 544/198 |
| 4,086,204 | 4/1978 | Cassandrini et al. | 544/198 |
| 4,108,829 | 8/1978 | Cassandrini et al. | 544/198 |
| 4,191,683 | 3/1980 | Brunetti et al. | 544/198 |
| 4,234,728 | 11/1980 | Rody et al. | 544/198 |
| 4,263,434 | 4/1981 | Cassandrini et al. | 544/198 |
| 4,315,859 | 2/1982 | Nikles | 544/198 |
| 4,321,374 | 3/1982 | Morimura et al. | 544/198 |
| 4,348,493 | 9/1982 | Loffelman | 544/198 |

FOREIGN PATENT DOCUMENTS

| | | |
|---|---|---|
| 2754 | 7/1979 | European Pat. Off. . |
| 14683 | 8/1980 | European Pat. Off. . |
| 22080 | 1/1981 | European Pat. Off. . |

*Primary Examiner*—John M. Ford
*Attorney, Agent, or Firm*—Connolly and Hutz

[57] ABSTRACT

The invention relates to new light stabilizers and heat stabilizers which have a low volatility and are migration-resistant, for use in organic polymers. They are obtained by reacting cyanuric halides with a monoamine containing piperidine groups and a polyamine component.

1 Claim, No Drawings

TRIAZINE STABILIZERS

The invention relates to new triazine compounds, a process for their preparation and their use as light stabilizers for organic polymers.

The new triazine compounds can be characterized by the general formula (I)

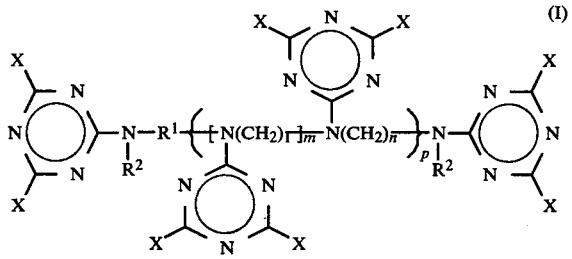

in which p is zero or 1, $R^2$ represents hydrogen, a $C_1$- to $C_6$-alkyl group, which can also be substituted by a hydroxyl group, or a group of the formula (II)

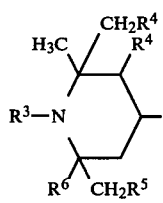

in which $R^3$ is hydrogen or $C_1$- to $C_{18}$-alkyl, preferably hydrogen or $C_1$- to $C_4$-alkyl, and in particular hydrogen, $R^4$ and $R^5$ are either identical and denote hydrogen or a $C_1$- to $C_5$-alkyl group, preferably hydrogen or a methyl group, and in particular hydrogen, in which case $R^6$ is a methyl group, or $R^4$ is hydrogen or $C_1$- to $C_5$-alkyl and $R^5$ and $R^6$, together with the carbon atoms to which they are bonded, represent a $C_5$- or $C_6$-cycloalkyl ring or a group of the formula

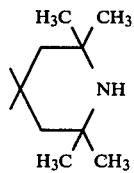

X denotes a group of the formula (III)

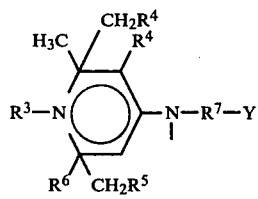

in which $R^3$, $R^4$, $R^5$ and $R^6$ have the meaning already given, $R^7$ represents an alkylene group which has 2 to 4 C atoms and can be substituted by a methyl group and Y represents a hydroxyl group or a group of the formula $-OR^8$ or $-N(R^9)_2$, in which $R^8 = C_1$- to $C_{18}$-alkyl and $R^9$ = methyl or ethyl, and, if p is zero, $R^1$ denotes an alkylene group or a dioxaalkylene group with 2 to 12, preferably 2 to 6, carbon atoms, or a methylaminodipropylene group, or a cycloalkylene group with 5 to 18 C atoms, or a cyclohexylene-dimethylene group, or a phenylene radical, which can be substituted by chlorine or methyl, or a dicyclohexylene or diphenylenemethane radical, which can be substituted by 2 methyl groups, or, together with the N atoms bonded to $R^1$, a piperazine group, in which case $R^2$ has no meaning, or a bis-(propylene)-piperazine group, whilst, if p=1 and m is an integer from 0 to 3, $R^1$ denotes an alkylene group of the formula $-(CH_2)_l-$, in which, in the case where m=0, the indices r and n can be identical or different and represent an integer from 2 to 6, preferably 2 or 3, but in the case where m=1, 2 or 3, the index l represents 2 or 3 and the indices r and n are identical and likewise represent 2 or 3.

Examples of the new compounds are:
1. N,N'-Bis-{2,4-[N-(2,2,6,6-tetramethyl-4-piperidyl)-3-dimethylaminopropylamino]-1,3,5-triazin-6-yl}-ethylenediamine
2. N,N'-Bis-(2,2,6,6-tetramethyl-4-piperidyl)-N,N'-bis-{2,4-[N-(2,2,6,6-tetramethyl-4-piperidyl)-3-dimethylaminopropylamino]-1,3,5-triazin-6-yl}-ethylenediamine
3. N,N'-bis{2,4-[N-(2,2,6,6-tetramethyl-4-piperidyl)-3-diethylaminopropylamino]-1,3,5-triazin-6-yl}-ethylenediamine
4. N,N'-Bis-(2,2,6,6-tetramethyl-4-piperidyl)-N,N'-bis-{2,4-[N-(2,2,6,6-tetramethyl-4-piperidyl)-3-diethylaminopropylamino]-1,3,5-triazin-6-yl}-ethylenediamine
5. N,N'-Bis-{2,4-[N-(2,2,6,6-tetramethyl-4-piperidyl)-3-dimethylaminopropylamino]-1,3,5-triazin-6-yl}-trimethylenediamine
6. N,N'-Bis-{2,4-[N-(2,2,6,6-tetramethyl-4-piperidyl)-3-diethylaminopropylamino]-1,3,5-triazin-6-yl}-trimethylenediamine
7. N,N'-Bis-{2,4-[N-(2,2,6,6-tetramethyl-4-piperidyl)-3-dimethylaminopropylamino]-1,3,5-triazin-6-yl}-hexamethylenediamine
8. N,N'-Bis-(2,2,6,6-tetramethyl-4-piperidyl)-N,N'-bis-{2,4-[N-(2,2,6,6-tetramethyl-4-piperidyl)-3-dimethylaminopropylamino]-1,3,5-triazin-6-yl}-hexamethylenediamine
9. N,N'-Bis-{2,4-[N-(2,2,6,6-tetramethyl-4-piperidyl)-3-diethylaminopropylamino]-1,3,5-triazin-6-yl}-hexamethylenediamine
10. N,N'-Bis-(2,2,6,6-tetramethyl-4-piperidyl)-N,N'-bis-{2,4-[N-(2,2,6,6-tetramethyl-4-piperidyl)-3-diethylaminopropylamino]-1,3,5-triazin-6-yl}-hexamethylenediamine
11. N,N'-Bis-{2,4-[N-(2,2,6,6-tetramethyl-4-piperidyl)-3-dimethylaminopropylamino]-1,3,5-triazin-6-yl}-dicyclohexylmethane-3,3'-diamine
12. N,N'-Bis-{2,4-[N-(2,2,6,6-tetramethyl-4-piperidyl)-3-diethylaminopropylamino]-1,3,5-triazin-6-yl}-dicyclohexylmethane-4,4'-diamine
13. N,N'-Bis-{2,4-[N-(2,2,6,6-tetramethyl-4-piperidyl)-3-diethylaminopropylamino]-1,3,5-triazin-6-yl}-diphenylmethane-4,4'-diamine
14. N,N'-Bis-{2,4-[N-(2,2,6,6-tetramethyl-4-piperidyl)-3-dimethylaminopropylamino]-1,3,5-triazin-6-yl}-3,3'-dimethyldicyclohexylmethane-4,4'-diamine
15. N,N',N''-Tris-{2,4-[N-(2,2,6,6-tetramethyl-4-piperidyl)-3-dimethylaminopropylamino]-1,3,5-triazin-6-yl}-diethylenetriamine 16. N,N',N''-Tris-{2,4-[N-(2,2,6,6-tetramethyl-4-piperidyl)-3-diethylaminopropylamino]-1,3,5-triazin-6-yl}-diethylenetriamine
17. N,N',N''-Tris-{2,4-[N-(2,2,6,6-tetramethyl-4-piperidyl)-3-dimethylaminopropylamino]-1,3,5-triazin-6-yl}-dipropylenetriamine
18. N,N',N''-Tris-{2,4-[N-(2,2,6,6-tetramethyl-4-piperidyl)-3-diethylaminopropylamino]-1,3,5-triazin-6-yl}dipropylenetriamine
19. N,N',N''-Tris-{2,4-[N-(2,2,6,6-tetramethyl-4-piperidyl)-3-dimethylaminopropylamino]-1,3,5-triazin-6-yl}-3-(2-aminoethyl)-aminopropylamine
20. N,N',N''-Tris-{2,4-[N-(2,2,6,6-tetramethyl-4-piperidyl)-3-diethylaminopropylamino]-1,3,5-triazin-6-yl}-3-(2-aminoethyl)-aminopropylamine
21. N,N',N'',N'''-Tetrakis-{2,4-[N-(2,2,6,6-tetramethyl-4-piperidyl)-3-dimethylaminopropylamino]-1,3,5-triazin-6-yl}-triethylenetetramine
22. N,N',N'',N'''-Tetrakis-{2,4-[N-(2,2,6,6-tetramethyl-4-piperidyl)-3-diethylaminopropylamino]-1,3,5-triazin-6-yl}-triethylenetetramine
23. N,N',N'',N'''-Tetrakis-{2,4-[N-(2,2,6,6-tetramethyl-4-piperidyl)-3-dimethylaminopropylamino]-1,3,5-triazin-6-yl}-tripropylenetetramine
24. N,N',N'',N'''-Tetrakis-{2,4-[N-(2,2,6,6-tetramethyl-4-piperidyl)-diethylaminopropylamino]-1,3,5-triazin-6-yl}-tripropylenetetramine
25. N,N',N''-Tris-{2,4-[N-(2,2,6,6-tetramethyl-4-piperidyl)-dimethylaminopropylamino]-1,3,5-triazin-6-yl}-bis-(6-aminohexyl)-amine
26. N,N',N'',N'''-Tetrakis-{2,4-[N-(2,2,6,6-tetramethyl-4-piperidyl)-dimethylaminopropylamino]-1,3,5-triazin-6-yl}-4,7-diazaundecane-1,11-diamine
27. N,N',N'',N'''-Tetrakis-{2,4-[N-(2,2,6,6-tetramethyl-4-piperidyl)-diethylaminopropylamino]-1,3,5-triazin-6-yl}-4,7-diazaundecane-1,11-diamine
28. N,N',N'',N''',$N^{IV}$-Pentakis-{2,4-[N-(2,2,6,6-tetramethyl-4-piperidyl)-dimethylaminopropylamino]-1,3,5-triazin-6-yl}-tetraethylenepentamine
29. N,N',N'',N''',$N^{IV}$-Pentakis-{2,4-[N-(2,2,6,6-tetramethyl-4-piperidyl)-diethylaminopropylamino]-1,3,5-triazin-6-yl}-tetraethylenepentamine
30. N,N',N'',N''',$N^{IV}$,$N^{V}$-Hexakis-{2,4-[N-(2,2,6,6-tetramethyl-4-piperidyl)-dimethylaminopropylamino]-1,3,5-triazin-6-yl}-pentaethylenehexamine
31. N,N',N'',N''',$N^{IV}$,$N^{V}$-Hexakis-{2,4-[N-(2,2,6,6-tetramethyl-4-piperidyl)-diethylaminopropylamino]-1,3,5-triazin-6-yl}-pentaethylenehexamine
32. N,N'-Bis-{2,4-[N-(2,2,6,6-tetramethyl-4-piperidyl)-diethylaminopropylamino]-1,3,5-triazin-6-yl}-1,3-bis-(aminomethyl)-cyclohexane
33. N,N'-Bis-{2,4-[N-(2,2,6,6-tetramethyl-4-piperidyl)-dimethylaminopropylamino]-1,3,5-triazin-6-yl}-bis-(3-aminopropyl)-piperazine
34. N,N'-Bis-{2,4-[N-(2,2,6,6-tetramethyl-4-piperidyl)-dimethylaminopropylamino]-1,3,5-triazin-6-yl}-4,7-dioxadecane-1,10-diamine
35. N,N'-Bis-{2,5-[N-(2,2,6,6-tetramethyl-4-piperidyl)-dimethylaminopropylamino]-1,3,5-triazin-6-yl}-4,9-dioxadodecane-1,12-diamine
36. N,N'-Bis-{2,4-[N-(2,2,6,6-tetramethyl-4-piperidyl)-diethylaminopropylamino]-1,3,5-triazin-6-yl}-7-methyl-4,10-dioxa-tridecane-1,13-diamine
37. N,N'-Bis-{2,4-[N-(2,2,6,6-tetramethyl-4-piperidyl)-3-hydroxypropylamino]-1,3,5-triazin-6-yl}-ethylenediamine
38. N,N'-Bis-{2,4-[N-(2,2,6,6-tetramethyl-4-piperidyl)-3-hydroxypropylamino]-1,3,5-triazin-6-yl}-hexamethylenediamine
39. N,N'-Bis-{2,4-[N-(2,2,6,6-tetramethyl-4-piperidyl)-3-ethoxypropylamino]-1,3,5-triazin-6-yl}-hexamethylenediamine
40. N,N'-Bis-{2,4-[N-(2,2,6,6-tetramethyl-4-piperidyl)-3-isoctyloxypropylamino]-1,3,5-triazin-6-yl}-hexamethylenediamine
41. N,N'-Bis-{2,4-[N-(2,2,6,6-tetramethyl-4-piperidyl)-3-octadecyloxypropylamino]-1,3,5-triazin-6-yl}-ethylenediamine
42. N,N'-Bis-{2,4-[N-(2,2,6,6-tetramethyl-4-piperidyl)-dimethylaminoethylamino]-1,3,5-triazin-6-yl}-ethylenediamine
43. N,N'-Bis-{2,4-[N-(2,2,6,6-tetramethyl-4-piperidyl)-4-diethylaminobutylamino]-1,3,5-triazin-6-yl}-hexamethylenediamine
44. N,N'-Bis-{2,4-[N-(2,2,6,6-tetramethyl-4-piperidyl)-4-diethylaminopropylamino]-1,3,5-triazin-6-yl}-aminoethylethanolamine
45. N,N'-Bis-{2,4-[N-(2,2,6,6-tetramethyl-4-piperidyl)-4-diethylaminopropylamino]-1,3,5-triazin-6-yl}-4-methylnonane-1,5,9-triamine
46. N,N'-Bis-{2,4-[N-(2,2,6,6-tetramethyl-4-piperidyl)-4-diethylaminopropylamino]-1,3,5-triazin-6-yl}-bis-(3-aminopropyl)-piperazine The new triazine stabilizers are obtained from cyanuric halides, it being possible to carry out the synthesis by two variants. According to variant A, a substituted triazine of the formula (III)

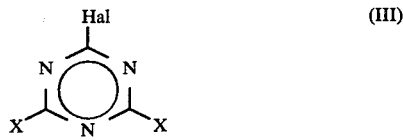

wherein Hal is halogen, preferably chlorine, and X has the abovementioned meaning, is first prepared by reacting 1 mole of a cyanuric halide with 2 moles of an amine of the formula (VI)

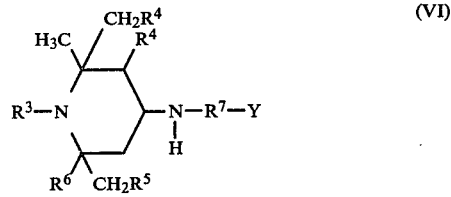

in which $R^3$, $R^4$, $R^5$, $R^6$, $R^7$ and Y have the abovementioned meaning and which is accessible in a manner corresponding to Example 17 of British Patent Specification No. 834,290. The product thereby obtained is then reacted with the equivalent amount, relative to the Hal, of a polyamine of the formula (IV)

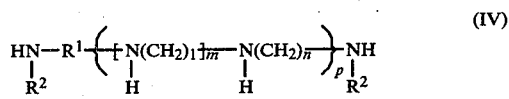

in which $R^1$, $R^2$, l, m, n and p have the abovementioned meanings.

According to variant B, which is particularly suitable for derivatives in which p=0, that is to say those obtained from diamines, a polyamine (IV) is first allowed to react with a cyanuric halide to give a compound of the formula (V)

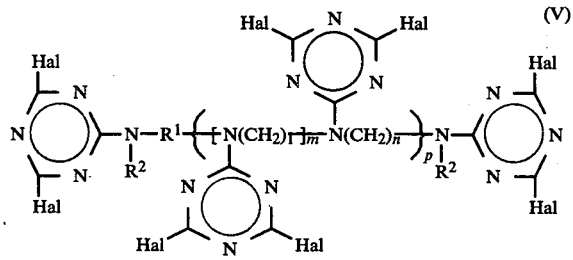

wherein Hal is halogen, but preferably chlorine, and $R^1$, $R^2$, l, m, n and p have the abovementioned meanings. This compound is then reacted with the equivalent amount, relative to the Hal, of a compound of the formula (VI).

A particularly simple procedure consists in not isolating the intermediate compounds (III) or (V), but especially not (III), at all at first, but, after they have been formed, allowing them to further react immediately with a polyamine of the formula (IV) or an amine of the formula (VI) in a so-called "one-pot process" to give the new triazine stabilizers.

Examples of amines of the formula (VI) are: (2,2,6,6-tetramethyl-4-piperidyl)-3-dimethylaminopropylamine, (2,2,6,6-tetramethyl-4-piperidyl)-3-diethylaminopropylamine, (2,2,6,6-tetramethyl-4-piperidyl)-3-hydroxypropylamine, (2,2,6,6-tetramethyl-4-piperidyl)-3-ethoxypropylamine, (2,2,6,6-tetramethyl-4-piperidyl)-3-isooctyloxypropylamine, (2,2,6,6-tetramethyl-4-piperidyl)-dimethylaminoethylamine and (2,2,6,6-tetramethyl-4-piperidyl)-4-diethylaminobutylamine.

Polyamines of the formula (IV) are, for example: ethylenediamine, propylenediamine, hexamethylenediamine, 1,12-diaminododecane, piperazine, bis-(3-aminopropyl)-piperazine, dicyclohexylmethane-3,3'-diamine, dicyclohexylmethane-4,4'-diamine, diphenylmethane-4,4'-diamine, 3,3'-dimethylcyclohexylmethane-4,4'-diamine, 1,3-bis-aminomethylcyclohexane, diethylenetetramine, 1,8,15-triaminopentadecane, 1,4,7,11-tetraaminoundecane, tetraethylenepentamine, pentaethylenehexamine, 4,7-dioxadecane-1,10-diamine and 4,9-dioxadodecane-1,12-diamine.

By cyanuric halides there are preferably understood the chlorides.

The reactions are carried out in organic solvents, such as, for example, petroleum ether, acetone, ether, dioxan, benzene, toluene, xylene, cymene, mesitylene and the like. In principle, two reaction steps at different temperatures are required.

The intermediate products (III) are thus prepared at 10° to 40° C. and reacted with the polyamines (IV) at 60° to 150° C., preferably at 80° to 150° C. If the intermediate product is a compound of the formula (V), it is expedient to carry out its preparation at 0° to 10° C. and then likewise to react it with the amine of the formula (VI) at 60° to 150° C., preferably at 80° to 150° C., to give the desired end products.

In all the reaction steps, it is necessary to add equivalent amounts, relative to the hydrogen halide formed, of a base, in particular an alkali metal hydroxide in solid form or aqueous solution. Suitable examples are sodium hydroxide, potassium hydroxide, sodium carbonate and potassium carbonate.

It was surprising, and could not be predicted, that it is possible to prepare the new compounds in the manner according to the invention. It had rather to be assumed that the reaction of cyanuric acid halides with primary or secondary monoamines or polyamines, which has been known for a long time and proceeds in accordance with the principle of synthesis of carboxylic acid amides from acid chlorides and amines [J. Am. Chem. Soc. 73 (1951), No. 7, page 2981 et seq.; U.S. Pat. No. 2,544,071; Swiss Patent Specification No. 342,784; and Swiss Patent Specification No. 342,785], would not proceed in a trouble-free manner in the present case. Since the key reaction for the preparation of the new compounds consists of the condensation between the unsubstituted or substituted cyanuric halide and the compound (VI)

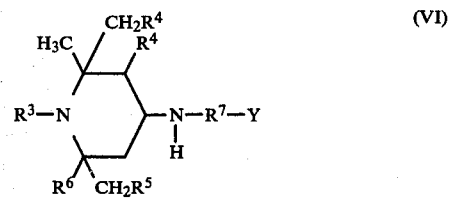

but this compound has an additional functional group Y, which can be —OH, —$OR^8$ or —$N(R^9)_2$ and which, analogously to the —NH— group, is likewise capable of undergoing reactions with acid chlorides, it was in fact to be expected that the compounds (VI) function as bridges between two different triazine rings, which would lead to undesired crosslinked products. Publications regarding the known formation of cyanuric acid esters from alcohols (Y=—OH), which, during the reaction, can also be formed from those compounds in which Y=—$OR^8$ by ether-splitting because of amounts of hydrogen halide which cannot be excluded, and regarding the synthesis of cyanuric acid dialkylamines from a cyanuric halide and tertiary amines, such as, for example, triethylamine, dialkylarylamines, alkylpiperidines and alkylmorpholines [Ullmann Volume 9 (1975), page 651; and E. Kober and R. Rätz, J. Org. Chem. 27 (1962), page 2509 et seq.] made such a course of the reaction appear entirely possible, if not even preferential.

The new triazine stabilizers can be incorporated without problems into the polymers to be stabilized and are outstandingly suitable for stabilizing these polymers against light-induced oxidative degradation.

Triazine compounds have already been proposed for stabilizing polymers (German Offenlegungsschriften Nos. 2,636,144 and 2,636,130 and Soviet Union Patent Specification No. 600,140), but it has been found that these compounds have diverse deficiencies. Thus, in evaluating the usefulness of a substance as a stabilizer, it is of great importance that, in addition to the activity, it has several other physical properties, in particular, for example, low volatility, compatibility with the polymers to be stabilized, resistance to migration in water, which plays a significant role in the case of weathering in the open, and also in hydrocarbons, a melting point which is below the processing temperature required for the plastic, and which is a prerequisite for uniform distribution of the stabilizer in the polymer, and the heat-stability of the additives even at the very high processing temperatures arising in some cases.

No substance is as yet known which, in all the points mentioned, would fulfil the requirements made of an outstanding stabilizer so that it can be used completely satisfactorily in practice, and the triazine compounds described in the abovementioned patent specifications are thus to be regarded only as compromise solutions with regard to their suitability as stabilizers. For these reasons, it is also understandable that none of these products has hitherto achieved commercial importance. At present, only bis-(2,2,6,6-tetramethyl-4-piperidyl) sebacate is employed on a relatively large scale as a light stabilizer (German Patent Specification No. 1,929,928 and German Offenlegungsschrift No. 2,204,659).

The triazine stabilizers of the invention are largely free from the abovementioned disadvantages and are distinguished by an exceptionally good activity as stabilizers for organic polymers. Thus, in spite of their enormous polarity, which is not least caused by the radical Y, their compatibility with the polymers to be stabilized is unexpectedly good, which is to be regarded as surprising, especially when they are used in non-polar polymers, such as polyethylene and polypropylene. Their low volatility compared with the best compound of the state of the art (Example 6 of German Offenlegungsschrift No. 2,636,144) was also not to be predicted, likewise because of the Y radical, which is in itself unstable to heat.

As already mentioned the new compounds are used as stabilizers for plastics to protect them from damage by the action of oxygen, heat and light. Specific examples of such plastics are:

Polymers which are derived from mono- or di-unsaturated hydrocarbons, for example polyolefins, such as polyethylene, which can optionally be cross-linked, polypropylene, polybut-1-ene, polyisobutene, polymethylbut-1-ene, polymethylpent-1-ene, polyisoprene, polybutadiene and polystyrene, copolymers of the monomers on which the homopolymers mentioned are based, such as ethylene/propylene copolymers, propylene/but-1-ene copolymers, propylene/isobutene copolymers and styrene/butadiene copolymers, and terpolymers of ethylene and propylene with a diene, such as, for example, hexadiene, dicyclopentadiene or ethylidenenorbornene; and mixtures of the abovementioned homopolymers, such as, for example, mixtures of polypropylene and polyethylene, polypropylene and polybut-1-ene and polypropylene and polyisobutylene, or of a butadiene/acrylonitrile copolymer and a styrene/butadiene copolymer.

Halogen-containing vinyl polymers, such as polyvinyl chloride, polyvinylidene chloride, polyvinyl fluoride, polychloroprene and chlorinated rubbers, as well as copolymers of vinyl chloride and vinylidene chloride with one another and with other olefinically unsaturated monomers.

Polymers which are derived from α,β-unsaturated acids and derivatives thereof, such as polyacrylates and polymethacrylates, polyacrylamides and polyacrylonitrile, and copolymers thereof with one another and with other vinyl compounds, such as acrylonitrile/butadiene/styrene copolymers, acrylonitrile/styrene copolymers and acrylonitrile/styrene/acrylate copolymers.

Polymers which are derived from unsaturated alcohols and amines or their acyl derivatives or acetals, such as polyvinyl alcohol, polyvinyl acetate, stearate, benzoate or maleate, polyvinylbutyral, polyallyl phthalate and polyallylmelamine, and copolymers thereof with other vinyl compounds, such as ethylene/vinyl acetate copolymers.

Homopolymers and copolymers which are derived from epoxides, such as polyethylene oxide, or the polymers which are derived from bisglycidyl ethers.

Polyacetals, such as polyoxymethylene and polyoxyethylene, and those polyoxymethylenes which contain ethylene oxide as a comonomer.

Polyurethanes and polyureas.

Polycarbonate.

Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.

Polyesters which are derived from dicarboxylic acids and dialcohols and/or from hydroxycarboxylic acids or the corresponding lactones, such as polyethylene terephthalate, polybutylene terephthalate and poly-1,4-dimethylol-cyclohexane terephthalate.

Crosslinked polymers which are derived from aldehydes on the one hand and phenols, ureas and melamines on the other hand, such as phenol/formaldehyde resins, urea/formaldehyde resins and melamine/formaldehyde resins.

The stabilization of polyolefins, styrene polymers, polyamides, poly(meth) acrylates and polyurethanes, for which the compounds are preferably suitable, is of particular importance. Examples of these polymers are high-density polyethylene and low-density polyethylene, polypropylene, ethylene/propylene copolymers, polystyrene, styrene/butadiene/acrylonitrile terpolymers, mixtures of polyolefins or of styrene polymers, and polyurethanes on a polyether or polyester basis.

The new stabilizers are incorporated into the polymer masses by generally customary methods. The incorporation can be effected, for example, by mixing the compounds, and, if appropriate, other additives, into the melt by the methods customary in the art before or after shaping, or by applying the dissolved or dispersed compounds onto the polymer direct or by mixing them into a solution, suspension or emulsion of the polymer, if necessary allowing the solvent subsequently to evaporate. The amounts are 0.01 to 5% by weight, preferaby 0.05 to 2.5 and in particular 0.1 to 1.0% by weight, relative to the material to be stabilized. The new compounds can also be added in the form of a master batch, which contains these compounds, for example, in a concentration of 2.5 to 50% by weight, preferably 5.0 to 20% by weight, to the plastics to be stabilized.

If appropriate, the plastics stabilized by adding the substances according to the invention can also contain other known and customary additives, such as, for example, antioxidants based on phenol or sulfide, UV absorbers and light stabilizers, phosphite stabilizers, metal compounds, epoxy stabilizers and polyhydric alcohols.

Examples of antioxidants are those of the sterically hindered phenol type, such as 4,4'-butylidene-bis-(2,6-di-tert.-butylphenol), 4,4'-thio-bis-(2-tert.-butyl-5-methylphenol) and phenolic triazine compounds, thiodipropionic acid esters of fatty alcohols and dioctadecyl sulfide and disulfide.

The UV absorbers and light stabilizers include, for example, 2-(2'-hydroxyphenyl)-benztriazoles, such as 2-(2'-hydroxy-5'-methylphenyl)-benztriazole, 2-hydroxybenzophenones, such as 2-hydroxy-4-octyloxybenzophenone, stabilizers from the salicylate group, such as octyl phenylsalicylate, nickel chelates, oxalic acid diamides and sterically hindered piperidine compounds.

Phosphites which may be mentioned are tris-nonylphenyl phosphite, tris-lauryl phosphite or esters of pentaerythritol phosphite.

By metal compounds known as stabilizers there are understood, in this connection: calcium, barium, strontium, zinc, cadmium, magnesium, aluminum and lead soaps of aliphatic carboxylic acids or hydroxycarboxylic acids with about 12 to 32 C atoms, salts of the metals mentioned with aromatic carboxylic acids, such as benzoates or salicylates, as well as (alkyl) phenolates of these metals, and also organo-tin compounds, such as, for example, dialkyl-tin thioglycolates and carboxylates.

Known epoxy stabilizers are, for example, epoxidized higher fatty acids, such as epoxidized soya bean oil, tall oil or linseed oil, or epoxidized butyl oleate, as well as epoxides of long-chain olefins.

Polyhydric alcohols can be, for example, pentaerythritol, trimethylolpropane, sorbitol or mannitol, that is to say preferably alcohols with 5 or 6 C atoms and 2 to 6 OH groups.

An effective stabilizer combination for poly-α-olefins, such as, for example, high-pressure, medium-pressure and low-pressure polymers of $C_2$- to $C_4$-α-olefins, in particular polyethylene and polypropylene, or of copolymers of such α-olefins, consists, for example, of—per 100 parts by weight of polymer—0.01 to 5 parts by weight of one of the compounds to be used according to the invention, 0.05 to 5 parts by weight of a phenolic stabilizer, if appropriate 0.01 to 5 parts by weight of a sulfur-containing co-stabilizer, if appropriate 0.01 to 3 parts by weight of a basic or neutral metal soap, such as, for example, calcium stearate or zinc stearate, if appropriate 0.1 to 5 parts by weight of a phosphite, and if appropriate 0.01 to 5 parts by weight of a known UV stabilizer from the group comprising alkoxyhydroxybenzophenones, 4-hydroxyphenylbenzotriazoles, benzylidene-malonic acid mononitrile esters and so-called quenchers, such as, for example, nickel chelates.

The plastics stabilized according to the invention can be used in the most diverse form, for example as films, fibers, tapes or profiles, or as binders for lacquers, adhesives or putty.

The following examples serve to illustrate the invention further. Examples 1 to 4 show the preparation of intermediate compounds of the formula (III), which are reacted further in Examples 5 to 8, whilst the synthesis of intermediatte products of the formula (V) is described in Examples 9 to 13, further reaction of these products being carried out according to Examples 14 to 21.

EXAMPLE 1

2,4-[N-(2,2,6,6-Tetramethyl-4-piperidyl)-3-diethylaminopropylamino]-6-chloro-1,3,5-triazine A solution of 92.2 g (0.5 mole) of cyanuric chloride in 500 ml of acetone is added dropwise to a solution of 269 g (1 mole) of (2,2,6,6-tetramethyl-4-piperidyl)-3-diethylaminopropylamine in 500 ml of acetone at 20° C. After stirring the mixture for 30 minutes, a solution of 40 g (1 mole) of NaOH and 100 ml of water is added at 20° C. and the mixture is subsequently stirred at 20° C. for 6 hours. The NaCl which has precipitated is filtered off and the filtrate is concentrated on a rotary evaporator at room temperature. The residue is dried over $CaCl_2$.

EXAMPLE 2

2,4-[N-(2,2,6,6-Tetramethyl-4-piperidyl)-4-diethylaminobutylamino]-6-chloro-1,3,5-triazine This substance is prepared analogously to Example 1 from 283 g (1 mole) of (2,2,6,6-tetramethyl-4-piperidyl)-4-diethylaminobutylamine and 92.2 g (0.5 mole) of cyanuric chloride.

EXAMPLE 3

2,4-[N-(2,2,6,6-Tetramethyl-4-piperidyl)-3-ethoxypropylamino]-6-chloro-1,3,5-triazine 48.4 g (0.2 mole) of (2,2,6,6-tetramethyl-4-piperidyl)-3-ethoxypropylamine are initially introduced into 100 ml of acetone. A solution of 18.5 g (0.1 mole) of cyanuric chloride and 250 ml of acetone is added dropwise to this mixture at 20° C. The mixture is stirred at 40° C. for 6 hours and the solvent is then evaporated off in vacuo in a rotary evaporator. The residue is taken up in toluene, the mixture is filtered and the filtrate is evaporated in a rotary evaporator. A solid resin remains.

Cl: found: 6.9%; calculated: 6.3%.

EXAMPLE 4

2,4-[N-(2,2,6,6-Tetramethyl-4-piperidyl)-3-dimethylaminopropylamino]-6-chloro-1,3,5-triazine This compound was prepared analogously to Example 1 from 241 g (1 mole) of (2,2,6,6-tetramethyl-4-piperidyl-3-dimethylaminopropylamine and 92.2 g (0.5 mole) of cyanuric chloride.

EXAMPLE 5

N,N'-Bis-{2,4-[(N-(2,2,6,6-tetramethyl-4-piperidyl)-3-diethylaminopropylamino]-1,3,5-triazin-6-yl}-ethylenediamine 26.0 g (0.04 mole) of the compound according to Example 1 are initially introduced into 100 ml of xylene. 1.2 g (0.02 mole) of ethylenediamine and 1.6 g (0.04 mole) of NaOH powder are added and the mixture is boiled for 15 hours, using a water separator, during which about 0.5 ml of water are separated off. The NaCl is then filtered off, the filtrate is evaporated on a rotary evaporator and the residue is dried at 180° C. under a high vacuum. A resinous solid product remains.

EXAMPLE 6

N,N'-Bis-{2,4-[N-(2,2,6,6-tetramethyl-4-piperidyl)-3-dimethylaminopropylamino]-1,3,5-triazin-6-yl}-trimethylenediamine This product was prepared analogously to Example 5, but with 1.5 g (0.02 mole) of 1,3-diaminopropane instead of ethylenediamine.

EXAMPLE 7

N,N',N'',N''',N''''-Pentakis-{2,4-[N-(2,2,6,6-tetramethyl-4-piperidyl)-diethylaminopropylamino]-1,3,5-triazin-6-yl}-tetraethylenepentamine The preparation of this compound is analogous to Example 5, with 32.5 g (0.05 mole) of the product according to Example 1 and 1.83 g (0.01 mole) of tetraethylenepentamine instead of ethylenediamine.

EXAMPLE 8

N,N'-Bis-{2,4-[N-(2,2,6,6-tetramethyl-4-piperidyl)-dimethylaminopropylamino]-1,3,5-triazin-6-yl}-4,9-dioxadodecane-1,12-diamine This compound is prepared analogously to Example 5 from 28.4 g (0.04 mole) of the compound according to Example 4, 3.5 g (0.02 mole) of 4,9-dioxadodecane-1,12-diamine and 1.6 g of NaOH powder. Melting point: 135° to 165° C.

EXAMPLE 9

N,N'-Bis-(2,4-dichloro-1,3,5-triazin-6-yl)-ethylenediamine

A solution of 15 g (0.25 mole) of ethylenediamine in 125 ml of cold acetone is added dropwise, at 0° to 5° C., to 92.2 g (0.5 mole) of cyanuric chloride, dissolved in 500 ml of acetone. The mixture is subsequently stirred for 30 minutes and a solution of 20 g (0.5 mole) of NaOH in 125 ml of water is then slowly added at 0° to 5° C. After stirring the mixture at the same temperature for four hours, it is diluted with 500 ml of ice-water and the solid is filtered off. The desired compound is obtained in the form of a white powder.

EXAMPLES 10 TO 13

The reaction of cyanuric chloride with diamines was carried out as in Example 9, in the molar ratio indicated in that example, the products described in the table below being formed.

| Example No. | Product | Diamine employed |
|---|---|---|
| 10 | N,N'—Bis-(2,4-dichloro-1,3,5-triazin-6-yl)-hexamethylenediamine | Hexamethylenediamine |
| 11 | N,N'—Bis-(2,2,6,6-tetramethyl-4-piperidyl)-N,N'—(2,4-dichloro-1,3,5-triazin-6-yl)-ethylenediamine | N,N'—Bis-(2,2,6,6-tetramethyl-4-piperidyl)-ethylenediamine |
| 12 | N,N'—Bis-(2,4-dichloro-1,3,5-triazin-6-yl)-1,3-bis-(aminomethyl)-cyclohexane | 1,3-Bis-(aminomethyl)-cyclohexane |
| 13 | N,N'—Bis-(2,4-dichloro-1,3,5-triazin-6-yl)-bis-(4-aminocyclohexyl)-methane | Bis-(4-aminocyclohexyl)-methane |

EXAMPLE 14 TO 21

These examples show the further reaction of intermediate products according to Examples 9 to 13 with monoamines to give the stabilizers listed on pages 4 to 9.

EXAMPLE 14

N,N'-Bis-{2,4-[N-(2,2,6,6-tetramethyl-4-piperidyl)-3-dimethylaminopropylamino]-1,3,5-triazin-6-yl}-ethylenediamine 8.9 g (0.025 mole) of the compound according to Example 9 and 24.1 g (0.1 mole) of (2,2,6,6-tetramethyl-4-piperidyl)-3-dimethylaminopropylamine are initially introduced into 100 ml of xylene. 4.0 g (0.1 mole) of NaOH powder are added and the resulting reaction mixture is boiled for 16 hours, using a water separator. The solution which remains is filtered and the solvent is then distilled off in vacuo at 150° C. A light-colored solid remains.

The following compounds were prepared analogously:

| | | Starting materials and amounts | | |
|---|---|---|---|---|
| Example No. | Compound No. | Compound according to Example .../g | Monoamine/g | Melting point (°C.) |
| 15 | 32 | 12/10.9 | analogous to Example 12 | 118 |
| 16 | 12 | 13/12.6 | (2,2,6,6-tetramethyl-4-piperidyl)-3-diethyl-aminopropylamine/26.9 | 115 |
| 17 | 4 | 11/15.9 | (2,2,6,6-tetramethyl-4-piperidyl)-3-diethyl-aminopropylamine/26.9 | 47 (SP) |
| 18 | 7 | 10/10.3 | (2,2,6,6-tetramethyl-4-piperidyl)-3-diethyl-aminopropylamine/26.9 | 78–81 |
| 19 | 43 | 10/10.3 | (2,2,6,6-tetramethyl-4-piperidyl)-4-diethyl-aminopropylamine/28.3 | 50–54 |
| 20 | 39 | 10/10.3 | (2,2,6,6-tetramethyl-4-piperidyl)-3-ethoxy-propylamine/23.0 | 39 (SP) |
| 21 | 41 | 9/8.9 | (2,2,6,6-tetramethyl-4-piperidyl)-3-octadecyl-oxypropylamine/46.6 | 34 (SP) |

SP = softening point

EXAMPLES 22 TO 31

These examples show the procedure in the "one-pot process".

EXAMPLE 22

N,N',N''-Tris-{2,4-[N-(2,2,6,6-tetramethyl-4-piperidyl)-3-diethylaminopropylamino]-1,3,5-triazin-6-yl}-diethylenediamine 26.9 g (0.1 mole) of (2,2,6,6-tetramethyl-4-piperidyl)-3-diethylaminopropylamine (monoamine) are initially introduced into 100 ml of toluene. A solution of 100 ml of toluene and 9.2 g (0.05 mole) of cyanuric chloride is added dropwise to this mixture at 20° to 30° C. 4.0 g (0.1 mole) of NaOH powder are then added and the mixture is subsequently stirred at 30° C. for 6 hours. 1.7 g (0.017 mole) of diethylenetriamine (polyamine) and 2.0 g (0.05 mole) of NaOH powder are then added, the mixture is boiled for a further 16 hours, using a water separator, the NaCl which has separated out is then filtered off hot and the solvent is removed from the residue in vacuo, at a final temperature of 150° C. A light-colored solid substance of melting point 146° C. remains.

EXAMPLES 23 TO 30

The procedure is analogous to that in Example 22, using the same monoamine.

| Example No. | Compound No. | Polyamine/g | Melting point (°C.) |
|---|---|---|---|
| 23 | 18 | Dipropylenetriamine/2.2 | 109 |
| 24 | 20 | 3-(2-Aminoethyl)-amino-propylamine/1.9 | 97 |
| 25 | 22 | Triethylenetetramine/1.8 | 119 |
| 26 | 27 | 4,7-Diazaundecane-1,11-diamine/2.2 | 120 |
| 27 | 44 | Aminoethylethanolamine/2.6 | 75 |
| 28 | 31 | Pentaethylenehexamine/1.9 | 90 |
| 29 | 45 | Bis-(3-aminopropyl)-methylamine/3.8 | 87 |
| 30 | 46 | Bis-(3-aminopropyl)-piperazine/5.0 | 83 |

EXAMPLE 31

N,N',N",N'''-Tetrakis-{2,4-[N-(2,2,6,6-tetramethyl-4-piperidyl)-3-dimethylaminopropylamino]-1,3,5-triazin-6-yl}-triethylenetetramine This compound is prepared analogously to Example 22 using 24.1 g of (2,2,6,6-tetramethyl-4-piperidyl)-3-dimethylaminopropylamine and 1.8 g of triethylenetetramine. A product with a melting point of 73° to 87° C. is obtained.

EXAMPLE 32

This example shows the volatility of the new triazine stabilizers compared with that of a product of the closest state of the art.

The volatilities were determined in an apparatus for thermogravimetric analysis. For this determination, equal amounts (500 mg) of the compounds according to the invention and of the comparison substance were heated up to 300° C. in a nitrogen atmosphere with a heating-up rate of 2K/minute, and the loss of substance was measured in mg/cm². The following table shows the results:

| Stabilizer according to Example | Weight loss in mg/cm² on reaching ... °C. | | | |
|---|---|---|---|---|
| | 220 | 260 | 300 | 10 minutes at 300 |
| 16 | 0.16 | 2.05 | 5.37 | 8.06 |
| 20 | 0.16 | 1.74 | 5.53 | 8.54 |
| 27 | 0.47 | 2.21 | 8.85 | 12.01 |
| Comparison* | 0.47 | 3.48 | 10.59 | 17.38 |

*Substance according to Example 6 of German Offenlegungsschrift 2,636,144 (reaction product of cyanuric chloride and N,N'—(2,2,6,6-tetramethyl-4-piperidyl)-hexamethylenediamine).

EXAMPLE 33

This example is intended to show the light-stabilizing action of the new compounds in poly-α-olefins.

100 parts by weight of polypropylene with a melt index i₅ of about 6 g/10 minutes (determined in accordance with the method of ASTM D 1238-62 T) and a density of 0.90 g/co were mixed with 0.1 part by weight of pentaerythritol tetrakis-3-(3,5-di-tert.-butyl-4-hydroxyphenyl)-propionate, 0.2 part by weight of calcium stearate and 0.1 part by weight of the stabilizer, according to the invention, to be tested.

In order to achieve as uniform a distribution as possible on the polymer granules, the stabilizers were dissolved in a solvent and the solution was added dropwise to the polypropylene powder, whilst stirring, most of the solvent being evaporated off again by simultaneous irradiation with a IR lamp.

After about 20 minutes, the calcium stearate was added and mixing was continued for a further 10 minutes. Residues of solvent were removed by drying at 50° C./120 minutes in a drying cabinet.

The polypropylene was injection-molded to 60×60×1 mm sheets at 240° C. in a Windsor Type SP 50 injection-molding machine. Test pieces in accordance with DIN 53,455, Shape 3, reduced in scale by 1:3, were stamped out of these sheets. The test pieces required as comparison samples were produced analogously, but with the stabilizers to be tested being left out and the comparison stabilizers being added.

To determine the stability to light, the samples were subjected to irradiation with alternating light in a Xenotest 1200 apparatus from Messrs. Original Hanau Quarzlampen GmbH. The radiation intensity was modulated by a UV filter (special filter glass d=1.7 mm). The stability to light was tested in accordance with the method of DIN 53,387 (17 minutes moistening, 3 minutes water-spraying, black-panel temperature of 45° C., atmospheric humidity of 70 to 75%). The exposure time in hours was measured and the elongation at break was determined on a tensometer from Messrs. Instron at a pulling speed of 5 cm/minute.

| Stabilizer according to Example | Exposure time in hours | Elongation at break determined, in % of the initial value |
|---|---|---|
| 16 | 1,400 | >50 |
| 20 | 1,400 | >50 |
| 27 | 1,400 | >50 |
| Polypropylene | 260 | 1 |
| Comparison[1] | 320 | 1 |
| Comparison[2] | 1,400 | 50 |

[1]without a stabilizer
[2]compound according to Example 6 of German Offenlegungsschrift 2,636,144

EXAMPLE 34

0.1 to 0.25 part by weight of the stabilizers given in Example 33 is mixed into polypropylene (®Hostalen PPU VP 1770 F from HOECHST AG) of melt index MFI 190/5:19 g/10 minutes, see DIN 53,535, using a high-speed laboratory mixer. The material thus stabilized was melted in a laboratory extruder under the customary processing conditions and processed via a spinning pump with a multi-orifice spinneret to give monofilaments (87 dtex), which were then subsequently stretched in the ratio 1:2.5. In each case 24 of these filaments were texturized to yarn and this yarn was worked into test fabrics. The test pieces were subjected to the light-fastness test in a fadeometer and, after the exposure time indicated, were subjected to the fingernail test (light rubbing of the thumbnail over the fabric). After an exposure time of 160 hours, the test fabrics stabilized with the compounds according to the invention were still undamaged.

We claim:
1. A triazine compound of the formula

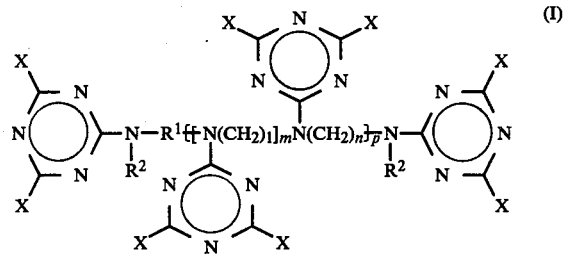

(I)

in which p is 1, R² represents hydrogen, a C₁- to C₆-alkyl group or a group of the formula

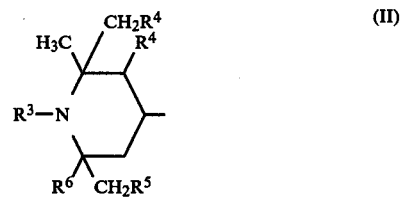

(II)

in which $R^3$ is hydrogen or $C_1$- to $C_{18}$-alkyl, $R^4$ and $R^5$ are either identical and are hydrogen or a $C_1$- to $C_5$-alkyl group, in which case $R^6$ is a methyl group, or $R^4$ is hydrogen or $C_1$- to $C_5$-alkyl, and $R^5$ and $R^6$, together with the carbon atoms to which they are bonded, represent a $C_5$- or $C_6$-cycloalkyl ring or a group of the formula

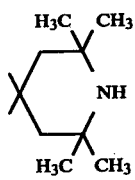

X is a group of the fomrula

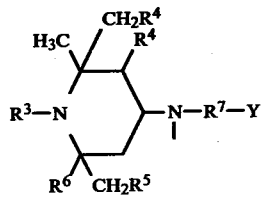

in which $R^3$, $R^4$, $R^5$ and $R^6$ have the meaning already given, $R^7$ represents an alkylene group which has 2 to 4 C atoms and can be substituted by a methyl group and Y represents a group of the formula $-OR^8$ or $-N(R^9)_2$, in which $R^8 = C_1$- to $C_{18}$-alkyl and $R^9$ = methyl or ethyl, with the proviso that $-R^7-Y$ is other than $-CH_2CH_2-OH$, and, $R^1$ is an alkylene group of the formula $-(CH_2)_r-$, in which, in the case where m=0, the indices r and n can be identical or different and represent an integer from 2 to 6, but in the case where m=1, 2 or 3, the index 1 represents 2 or 3 and the indices r and n are identical and likewise represent 2 or 3.

* * * * *